US00PP32715P3

(12) United States Plant Patent
Randag

(10) Patent No.: US PP32,715 P3
(45) Date of Patent: Dec. 29, 2020

(54) CALLA LILY PLANT NAMED 'A405'

(50) Latin Name: *Zantedeschia aethiopica*
Varietal Denomination: A405

(71) Applicant: Dümmen Group B.V., De Lier (NL)

(72) Inventor: Cecilius Jan-Jochem Randag, CJ 'T Zand (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,413

(22) Filed: Sep. 30, 2019

(65) Prior Publication Data

US 2020/0113101 P1 Apr. 9, 2020

Related U.S. Application Data

(60) Provisional application No. 62/766,213, filed on Oct. 5, 2018.

(51) Int. Cl.
*A01H 5/02* (2018.01)
*A01H 6/10* (2018.01)

(52) U.S. Cl.
USPC ..... Plt./490
CPC ..... *A01H 6/10* (2018.05)

(58) Field of Classification Search
USPC ..... Plt./490
CPC ..... A01H 5/02
See application file for complete search history.

*Primary Examiner* — Kent L Bell
(74) *Attorney, Agent, or Firm* — The Webb Law Firm

(57) ABSTRACT

'A405' is a new variety of calla lily plant having white colored spathes that produces 6-10 inflorescences per 16-18 cm tuber. The flower stems are about 30-40 cm in height. The leaves are green with numerous whitish spots and have a leathery texture.

1 Drawing Sheet

Botanical classification: *Zantedeschia aethiopica.*
Varietal denomination: 'A405'.

BACKGROUND OF THE NEW PLANT

The present invention comprises a new and distinct cultivar of calla lily, botanically known as *Zantedeschia aethiopica* and hereinafter referred to by the cultivar name 'A405'.

'A405' is a product of a planned breeding program, which had the objective of creating *Zantedeschia* hybrids for pot flower production in a wide range of colors with a large, classic flower shape. The breeding program began in 2007, and the new cultivar is a seedling selected from the crossing of *Zantedeschia aethiopica* seedling A080017-211 (female parent, unpatented) with *Zantedeschia aethiopica* seedling A090001-3 (male parent, unpatented). 'A405' was selected in 2014 by the inventor in 't Zand, The Netherlands as one flowering plant within the progeny of the stated cross.

The first act of asexual reproduction of 'A405' by tissue culture was performed by the inventor in September of 2014 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown from 12 to 14 weeks in 14 cm pots in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'A405' which, in combination, distinguish this calla lily as a new and distinct cultivar:

1. Compact plant habit;
2. Numerous leaf maculations; and
3. High inflorescence production.

Table 1 provides a comparison of 'A405' to its parents, as well as *Zantedeschia aethiopica* variety 'Colombe de la Paix' (unpatented).

TABLE 1

| Variety | Relationship | Trait differences | Description |
|---|---|---|---|
| 'A405' | New variety | Spathe color | RHS 155B |
| | | Plant height | 30-40 cm |
| A080017-211 | Female parent | Plant height | 33-45 cm |
| A090001-3 | Male parent | Spathe color | RHS 187A |
| | | Plant height | 40-55 cm |
| 'Colombe de la Paix' | Known variety | Plant height | 60-150 cm |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Deciduous.

Size:

*Height of the leaf canopy above the soil.*—25-35 cm.

*Height of top of inflorescences above the soil.*—30-40 cm.

*Diameter.*—6-15 cm.

Form: Spreading.

Number of inflorescences per tuber:

*Size* 16-18 cm in diameter.—6-10 inflorescences.

Branches:

*Number.*—Plentiful.

*Color.*—Between Green Group RHS 137B and 137C.

*Young shoot color.*—Between Purple Group RHS N77A and N77C.

Leaves:

*Size.*—Width: 2-9 cm, with the broadest part of the leaf blade far below the middle. Length: 6-20 cm.

*Number per plant.*—15-55.

*Leaf blade lobes.*—Present; having a length of 0.5-2.5 cm.

*Shape.*—Ovate to slightly sagittate.

*Apex.*—Apiculate.

*Base.*—Rounded.

*Margin.*—Entire; having a color of Green Group RHS 138A to 138B.

*Color.*—Upper surface: Green Group RHS 137B to 137C, with numerous White Group RHS 155C maculations present. Lower surface: Green Group RHS 137B to Yellow-Green Group RHS 146B, with numerous White Group RHS 155D maculations present.

*Veins.*—Configuration: Pinnate. Color: Green Group RHS 138A to 137B.

*Surface texture.*—Smooth (both surfaces).

*Petiole.*—Length: 8-20 cm. Diameter: 11 mm. Color: The base is Purple Group RHS N77A to RHS 77C, the upper part is Yellow-Green Group RHS 144A.

Roots:

*Color.*—White Group RHS 155D.

*Branching description.*—Fibrous root system. Several main roots emerge from the top of the tuber and form a small number of lateral roots.

Spathe:

*Size.*—Length (measured from opening to tip): 9-12 cm. Width: 4-10 cm. Height: 4-8 cm.

*Color.*—Throat spot: Absent. Upper surface: White Group RHS 155B. Lower surface: White Group RHS 155B.

*Vein color.*—Black Group RHS 202C to 202D.

*Shape.*—Funnel.

*Apex.*—Acuminate.

*Base.*—Attenuate.

*Margin.*—Entire.

Spadix:

*Shape.*—Cylinder.

*Size.*—Length: 40-60 mm. Diameter: 5-7 mm.

*Color.*—Yellow Group RHS 13A to 13B.

*Position relative to spathe.*—Upright.

*Female flower.*—Number: 20-40. Shape: Pyramid. Height: 6 mm. Diameter: 5 mm.

*Male flower.*—Number: 120-180. Shape: Cone. Height: 5 cm. Diameter: 5 mm.

Peduncle:

*Size.*—Length: 25-35 cm. Diameter: 10-15 mm.

*Color.*—The upper part is Yellow-Green Group RHS 144A, the lower part is Yellow-Green Group RHS 144A to 144C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Abundant; similar to 'Picasso' (U.S. Plant Pat. No. 15,282). Color: Between White Group RHS 155B and 155C.

*Anther.*—Shape: Round. Length: Less than 1 mm. Color: Between Yellow Group RHS 13A and 13B.

*Filament.*—Length: Less than 1 mm. Color: Between White Group RHS 155C and 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 8B and 8C.

*Ovaries.*—Texture: Smooth. Length: Between 1 to 10 mm. Width: Between 1 to 10 mm. Color: The top color is Yellow-Green Group RHS N144B to N144C, the bottom color is Yellow-Green Group RHS 150B.

Seeds:

*Length.*—1-3 mm.

*Width.*—2-4 mm.

*Color.*—Greyed-Orange Group RHS 177B to 177D.

*Number.*—1-150.

Disease resistance: No unusual susceptibility/resistance to diseases noticed to date.

Pest resistance: No unusual susceptibility/resistance to pests noticed to date.

Heat tolerance: No heat tolerance.

Hardiness: Not hardy.

Lastingness: About one week on the plant.

Fragrance: Light and sweet.

I claim:

1. A new and distinct variety of calla lily plant named 'A405' as herein described and illustrated.

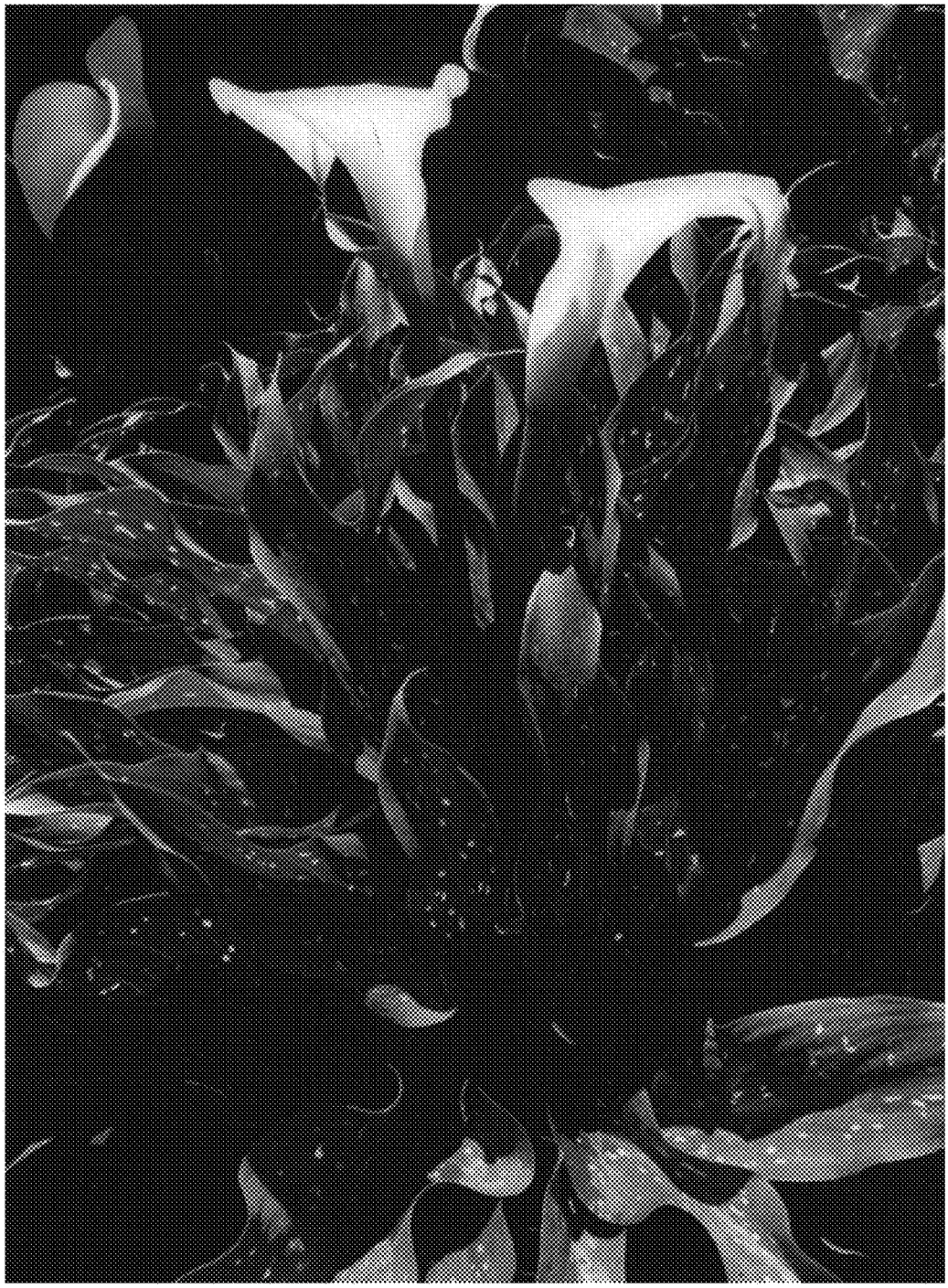

* * * * *